(12) United States Patent
Penza et al.

(10) Patent No.: US 7,551,197 B2
(45) Date of Patent: Jun. 23, 2009

(54) PIPELINE INSPECTION SYSTEM

(75) Inventors: G. Gregory Penza, Huntington, NY (US); George Lohr, Commack, NY (US); Hermann Herrlich, Lindenhurst, NY (US)

(73) Assignee: ULC Robotics, Inc., Deer Park, NY (US)

( * ) Notice: Subject to any disclaimer, the term of this patent is extended or adjusted under 35 U.S.C. 154(b) by 331 days.

(21) Appl. No.: 11/222,086

(22) Filed: Sep. 8, 2005

(65) Prior Publication Data

US 2007/0051192 A1   Mar. 8, 2007

(51) Int. Cl.
G03B 37/02 (2006.01)
F16L 55/30 (2006.01)
F16L 55/46 (2006.01)

(52) U.S. Cl. .......................................... 348/84; 396/19

(58) Field of Classification Search ..... 73/865.8–865.9, 73/866.5; 137/559; 138/103; 348/84; 396/19
See application file for complete search history.

(56) References Cited

U.S. PATENT DOCUMENTS

| | | | |
|---|---|---|---|
| 3,270,641 A * | 9/1966 | Gosselin .................. | 396/19 X |
| 3,667,359 A | 6/1972 | Watts et al. | |
| 3,718,978 A | 3/1973 | VanKoevering et al. | |
| 3,832,724 A * | 8/1974 | Duval ....................... | 396/19 |
| 4,134,453 A * | 1/1979 | Love et al. ................. | 166/298 |
| 4,302,772 A | 11/1981 | Gillot | |
| 4,677,472 A | 6/1987 | Wood | |
| 4,704,897 A | 11/1987 | Kawase et al. | |
| 5,025,670 A * | 6/1991 | McNulty et al. ........... | 73/865.8 |
| 5,195,392 A | 3/1993 | Moore et al. | |
| 5,329,824 A | 7/1994 | Carapezza et al. | |
| 5,604,532 A | 2/1997 | Tillmanns | |
| 5,611,283 A | 3/1997 | Cotton et al. | |
| 5,612,499 A | 3/1997 | Andrew et al. | |

(Continued)

FOREIGN PATENT DOCUMENTS

CA   2428551 A1 * 11/2003

(Continued)

OTHER PUBLICATIONS

Aries Industries, Inc., "GasCam Video Inspection System"; retrieved on May 22, 2002, from URL:http://www.ariesind.com/gascam.html; 2 pages.

*Primary Examiner*—Thomas P Noland
(74) *Attorney, Agent, or Firm*—Brooks Kushman P.C.

(57) ABSTRACT

An inspection system configured for "no-blow" use in a pressurized gas pipeline includes a push rod wound around a spool for convenient deployment and portability. A camera disposed on one end of the push rod is configured to relay images back to a monitor. A motor is configured for remote actuation by an operator, and provides for self-propelled movement of the camera in the pipeline. An entry tube is configured for sealed entry into the pipeline to facilitate entry of the camera and push rod. A guide shoe at the end of the entry tube provides a smooth transition for the camera and push rod as it leaves the entry tube and enters the pipeline. An automatically deployable and retractable positioning system is used to keep the camera away from an interior surface of the pipeline, and in the case of smaller pipelines, centers the camera within the pipeline.

10 Claims, 3 Drawing Sheets

U.S. PATENT DOCUMENTS

| | | |
|---|---|---|
| 5,654,795 A | 8/1997 | Dierlam |
| 5,754,220 A | 5/1998 | Smalser, Sr. |
| 5,956,077 A | 9/1999 | Qureshi et al. |
| 6,028,719 A | 2/2000 | Beckstead et al. |
| 6,111,600 A | 8/2000 | McLeod et al. |
| 6,259,523 B1 | 7/2001 | Welker |
| 6,313,869 B1 | 11/2001 | Hyp et al. |
| 6,338,359 B1 | 1/2002 | Welker |
| 6,359,645 B1 | 3/2002 | Sivacoe |
| 6,538,732 B1 | 3/2003 | Drost et al. |
| 6,621,516 B1 * | 9/2003 | Wasson et al. ............... 348/84 |
| 6,699,324 B1 * | 3/2004 | Berdin et al. ............. 118/306 |
| 6,958,767 B2 * | 10/2005 | Olsson et al. ............ 348/84 X |
| 7,137,308 B2 * | 11/2006 | Harris ...................... 73/865.8 |
| 7,143,659 B2 * | 12/2006 | Stout et al. ............... 73/865.8 |
| 7,179,019 B2 * | 2/2007 | Seto et al. ............... 405/183.5 |
| 7,181,985 B2 * | 2/2007 | MacMillan et al. ........ 73/865.8 |
| 7,191,673 B2 * | 3/2007 | Thornhill et al. .......... 73/865.8 |
| 2002/0003584 A1 | 1/2002 | Kossin |
| 2002/0113870 A1 * | 8/2002 | Mueckl et al. ................ 348/84 |
| 2002/0190682 A1 | 12/2002 | Schempf et al. |
| 2004/0006448 A1 | 1/2004 | Penza |
| 2004/0083829 A1 | 5/2004 | Chapman et al. |

FOREIGN PATENT DOCUMENTS

| | | | |
|---|---|---|---|
| EP | 450814 A1 * | 10/1991 | |
| EP | 511934 A1 * | 11/1992 | |
| GB | 2021351 A * | 11/1979 | |
| JP | 05141584 A * | 6/1993 | |
| JP | 06006920 A * | 1/1994 | |
| WO | WO 9114127 A * | 9/1991 | |

* cited by examiner

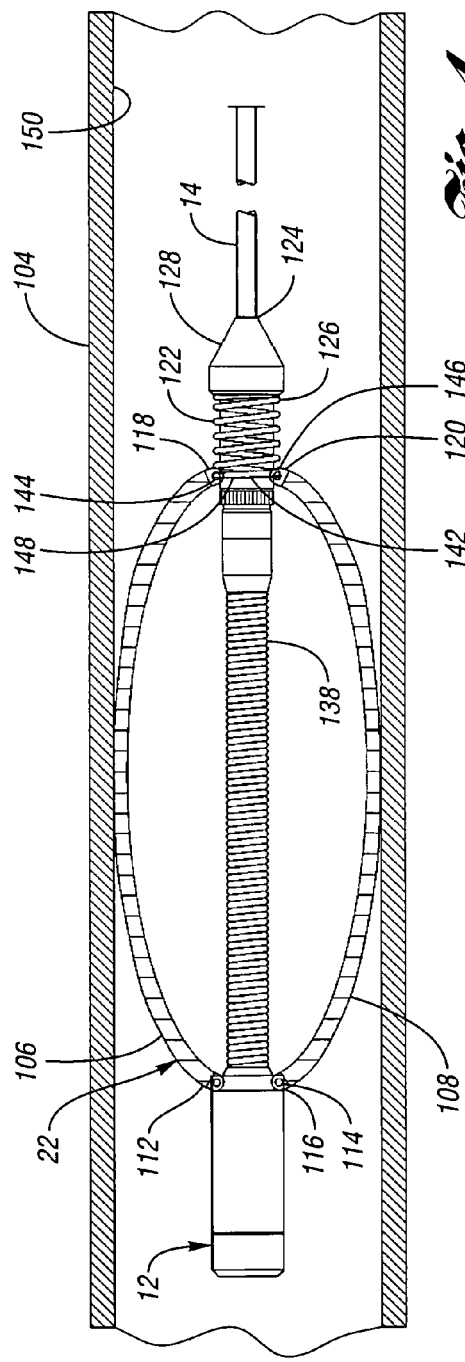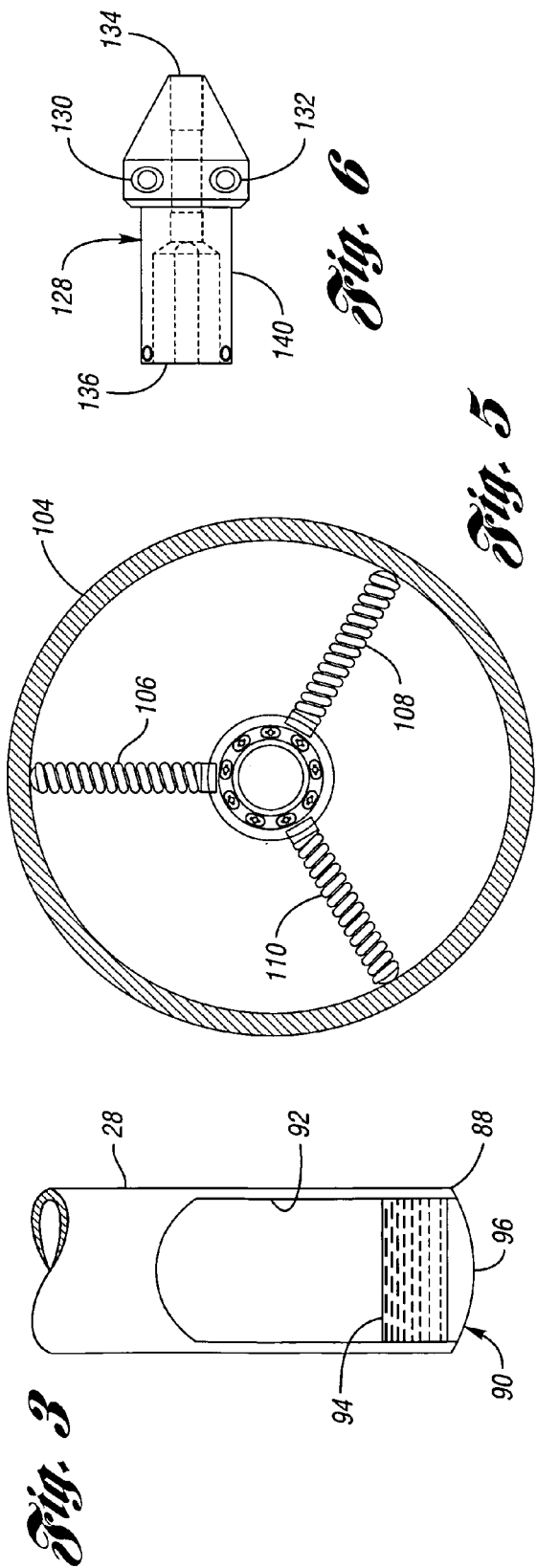

PIPELINE INSPECTION SYSTEM

BACKGROUND OF THE INVENTION

1. Field of the Invention

The present invention relates to a pipeline inspection system.

2. Background Art

For more than 30 years, video inspection has been a baseline fundamental analytical tool for the evaluation and assessment of pipeline integrity. Originally developed as an aid for sewer system maintenance, video inspection equipment and techniques have played a key role in the development of "no-dig" and "trenchless" pipeline rehabilitation methods. This is because the choice of the best trenchless rehabilitation method, for any given application, is often largely based on the video inspection that takes place prior to the rehabilitation. Thus, the information gleaned from the pre-rehabilitation video inspection is used as the basis for key decisions that drive the entire rehabilitation process.

The inspection of pipes often falls into two broad categories: inspections performed for purposes of preventative maintenance, and inspections performed as a response to a need for repair maintenance. The former category may include such things as locating cracks in the pipeline prior to their reaching a critical length, discovering the location of unknown branches or service tees, determining the exact location of valves and fittings, and finding water within the pipeline. In general, video inspection equipment is useful as a proactive tool for assessing the cleanliness, corrosion, and structural integrity of the pipeline. In the case of repair maintenance, high quality video inspection data is also very important. Indeed, the very nature of repair maintenance is such that it may include responding to emergency situations, particularly where hazardous materials are involved. Thus, the importance of quality video inspection equipment and techniques is further underscored.

One attempt to provide a pipe inspection system that can be used in a gas pipeline is described in U.S. Pat. No. 5,195,392 (Moore et al.). Moore et al. describes an inspection system for a pipeline that utilizes a camera head at the end of a snake which is fed down the pipeline to capture images at a desired location. The inspection system of Moore et al. requires two operators: one to feed the snake and camera head down the pipeline, and a second to view the images captured by the camera and provide instructions to the operator moving the camera. The snake is wound around a drum, and uncoiled by the first operator as the camera is manually fed down the pipeline. Moore et al. does note that some commercially available snakes may have electrically powered drum rotation. The camera may be provided with a number of centralizing members which are used to keep the camera approximately centered within the cross-section of the pipeline. After the camera is inserted in the pipeline, a curved tube can be positioned about the snake within the pipeline, and clamped in place.

One limitation of the pipeline inspection system described in Moore et al. is that it requires two operators to perform the inspection task. The first is required to feed the snake and camera down the pipeline, while the second is required to view the images from the camera and direct positioning of the camera by the first operator. In addition, the first operator is required to remain in close proximity to the opening of the pipeline, which may be undesirable if the pipeline is carrying pressurized gas. Although Moore et al. does contemplate the use of a motorized snake drum, an operator is still required to feed the snake down the pipeline under the direction of the second operator. Another limitation of the inspection system described in Moore et al. is that the camera must be placed through an opening in the pipeline prior to the opening being sealed by placement of the curved tube and its associated gasket. Thus, the opening to the pipeline remains unsealed until the camera head and a portion of the snake are inserted. This may be particularly undesirable when inspecting a high-pressure gas pipeline.

Therefore, a need exists for an inspection system that can be used to inspect a high-pressure gas pipeline, and that can be installed under sealed conditions so that seals are in place before the inspection apparatus is inserted into the pipeline. It would also be desirable to have a pipeline inspection system that would allow a single operator to control a camera from a location away from the pipeline opening, particularly where the pipeline is a high-pressure gas pipeline. In addition, it would also be desirable to have a pipeline inspection system with a camera having a positioning system which automatically deploys and retracts upon insertion and retraction of the camera, without the need for manual manipulation of the positioning system by an operator.

SUMMARY OF THE INVENTION

The present invention provides a pipeline inspection system which can used by a single operator, and can be used in a high-pressure gas pipeline and installed under sealed conditions to inhibit the escape of gas from inside the pipeline. At least one embodiment of the present invention includes an entry tube configured for insertion into the pipeline prior to insertion of a camera and push rod. The invention also provides a positioning system for the camera which is automatically deployable as it exits the entry tube and enters the pipeline. Further, the positioning system is automatically retractable as it is removed from the pipeline and enters the entry tube.

The invention further provides an inspection system for inspecting a pressurized gas pipeline that includes an elongate flexible guide member and a first conduit having first and second ends. The conduit is configured for sealed insertion into the pipeline such that the first end is outside the pipeline, the second end is inside the pipeline, and escape of gas from inside the pipeline is inhibited as the second end is inserted into the pipeline. The first conduit is further configured to receive the guide member therein, which facilitates entry of the guide member into the pipeline. A first seal cooperates with the first conduit and the guide member to inhibit gas from the pipeline from escaping through an inside of the first conduit. A transition member is located adjacent to the second end of the conduit for facilitating a change in direction of the guide member as the guide member enters the pipeline from within the conduit. A camera is attached to the guide member, and it is configured to pass through the conduit and into the pipeline.

The invention also provides an inspection system for a pressurized pipeline having an interior with a first diameter. The inspection system includes an elongate flexible guide member having a first end configured for entry into the pipeline. An entry tube is configured for insertion into the pipeline, thereby providing access to the interior of the pipeline for the guide member. A camera has first and second ends, and is disposed adjacent the first end of the guide member. The camera is configured to pass through the entry tube and into the pipeline. A biasing member is disposed between the first end of the guide member and the camera. The biasing member has a first end axially fixed relative to the first end of the guide member. The biasing member also has a second end axially movable relative to the first end of the guide member. The inspection system also includes at least two flexible arms, each of which has a first end pivotally disposed proximate to one of the ends of the camera. Each of the arms also has a second end pivotally disposed proximate to the second end of the biasing member. This facilitates automatic outward movement of a portion of each of the arms as the second end of the biasing member moves away from the first end of the biasing member when the arms exit the entry tube into the pipeline interior. This also facilitates inward movement of a portion of each of the arms when the arms are retracted into the entry tube, thereby causing a movement of the second end of the biasing member toward the first end of the biasing member.

The invention further provides an inspection system for a pressurized pipeline which defines a first longitudinal axis. The inspection system includes an elongate flexible guide member, and a first conduit having first and second ends and defining a second longitudinal axis. The first conduit is configured for insertion into the pipeline, and further configured to receive the guide member therein to facilitate entry of the guide member into the pipeline. A camera is attached to the guide member and configured to pass through the first conduit into the pipeline. A motor arrangement is disposed proximate the first end of the conduit, and is operable to move the guide member through the first conduit and into the pipeline. A transition member is located adjacent the second end of the first conduit, and has a first surface forming an oblique angle with the first longitudinal axis, and further forming an oblique angle with the second longitudinal axis. The first surface facilitates a change in direction of the guide member as the camera contacts the first surface of the transition member.

BRIEF DESCRIPTION OF THE DRAWINGS

FIG. 3 is a fragmentary view of a portion of an entry tube and guide shoe for the inspection system shown in FIG. 1;

FIG. 4 is a partial fragmentary view of a portion of the guide system shown in FIG. 1, including a positioning system deployed within a pipeline;

FIG. 5 is a front plan view of the pipeline and positioning system shown in FIG. 4; and FIG. 6 is a side plan view showing details of an adapter member shown in FIG. 4.

DETAILED DESCRIPTION OF THE PREFERRED EMBODIMENT(S)

Figure 1:
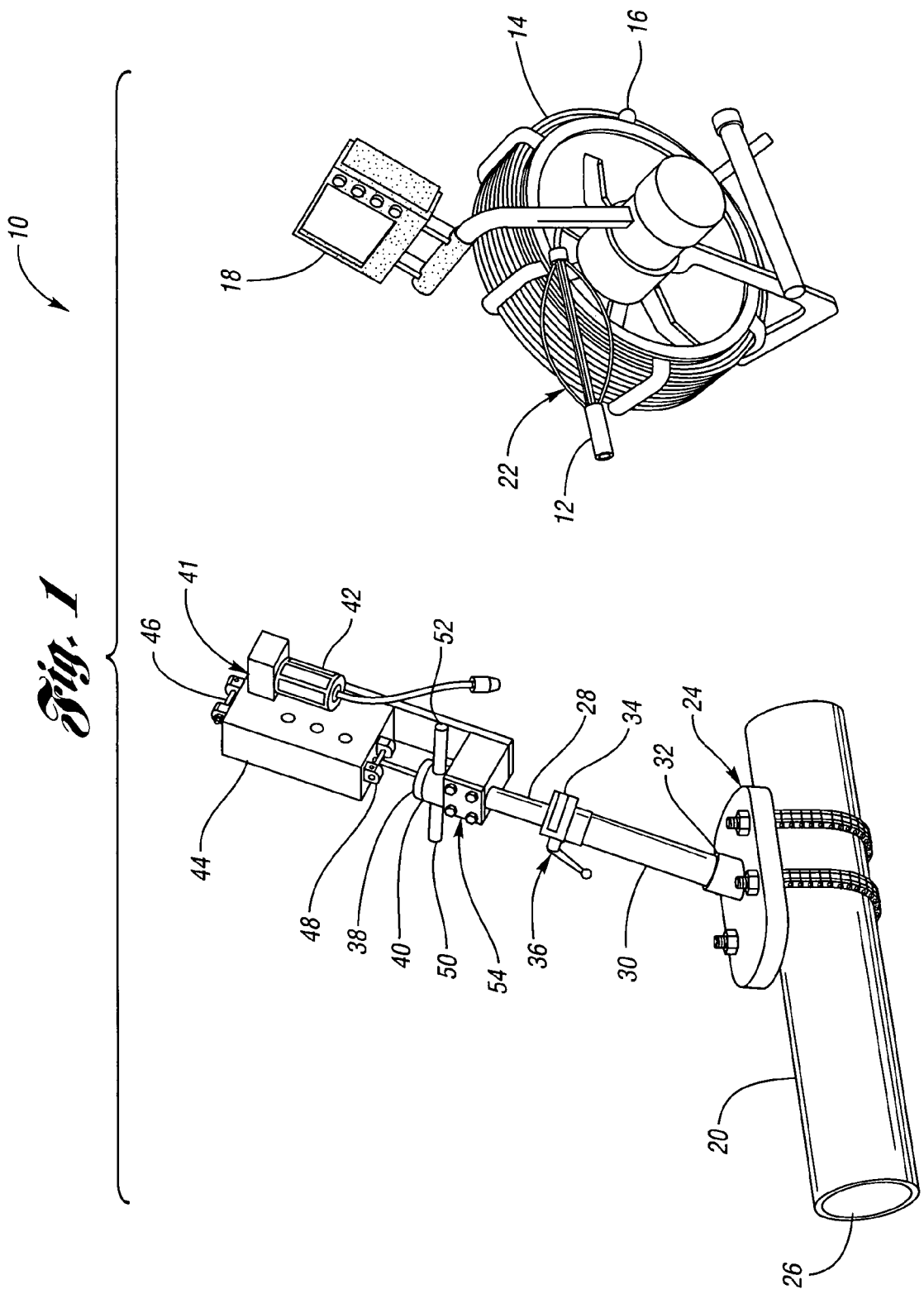
FIG. 1 is a partial schematic perspective view of one embodiment of an inspection system in accordance with the present invention.

FIG. 1 shows a partially schematic perspective view of a pipeline inspection system 10 in accordance with one embodiment of the present invention. The inspection system 10 includes a camera 12 which is attached to an elongate flexible guide member, or push rod 14. The push rod 14 is wound around a spool 16, which has a video display monitor 18 conveniently attached thereto. The monitor 18 is electrically connected to the camera 12, for providing images from inside a pipeline 20. As explained in detail below, a positioning system 22 is disposed between the camera 12 and the push rod 14 for positioning the camera 12 within a pipeline, such as the pipeline 20.

The pipeline 20 may be a high-pressure gas pipeline, for example, containing gas at 60 pounds per square inch (psi). To facilitate entry into the pipeline 20, a valve system 24 is used to provide selective access to an opening 25 in the pipeline 20. Any valve system that provides access to an interior 26 of the pipeline 20 through the opening 25 may be used. One example of such a valve system is the valve system commercially available from ALH Systems Limited. As an alternative, a fitting made from polyethylene, or another polymeric material or materials, could be attached to the pipeline 20, for example, by electrofusion. Other fittings could also be used, for example, a metal nipple could be welded to the pipeline.

Figure 2:
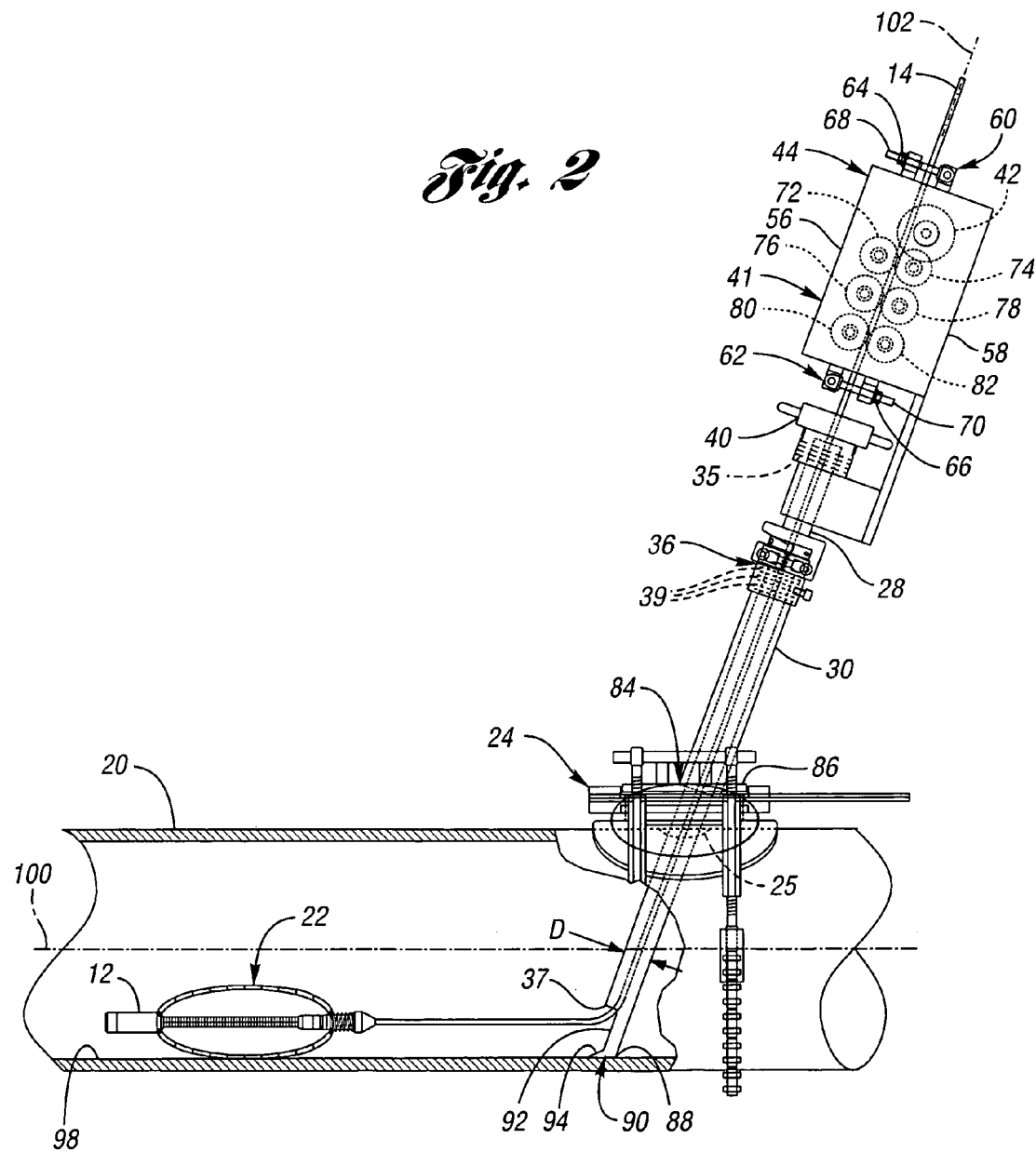
FIG. 2 is a partial fragmentary view of a portion of the inspection system shown in FIG. 1.

Once a fitting is attached to the pipeline 20, a drill (not shown) having a sealed attachment to the fitting, could be used to create the opening 25. The inspection system 10 also includes a first conduit, or entry tube 28, which facilitates entry of the camera 12 and push rod 14 into the pipeline 20. A second conduit 30 has a first end 32 which is configured for attachment to the valve system 24. As shown in FIG. 2, the second conduit 30 is attached to the pipeline 20 through the valve system 24. The second conduit 30 also has a second end 34 having a retaining structure, or clamp arrangement 36, attached thereto. The clamp arrangement 36 allows the entry tube 28 to be moved up and down to accommodate different pipeline diameters. Once the entry tube is properly positioned, the clamp arrangement 36 secures the entry tube 28 in place while the pipeline 20 is inspected.

The inspection system 10 is configured for "no-blow" use on pressurized pipelines, such as the pipeline 20. This means that the inspection system 10 is configured to reduce to a minimum, or completely eliminate, the escape of gas from a pipeline on which it is being used. The entry tube 28 has a first end 38 which has a cap 40 attached thereto. The cap 40 contains a first seal, or packing gland 35. The packing gland 35 cooperates with the entry tube 28 and the push rod 14 to provide a seal around the push rod 14 when it is inserted into the pipeline 20. The packing gland 35 inhibits gas from the pipeline 20 from escaping through the inside 37 of the entry tube 28. In addition, a second seal, made up of three O-rings 39, cooperates with the entry tube 28 and the second conduit 30 to provide sealed insertion of the entry tube 28 into the pipeline 20. Although the seals 35, 39 are shown as a packing gland and O-rings, respectively, it is understood that the use of different types of sealing structures is contemplated by the present invention. Moreover, although the packing gland 35 and the O-rings 39 are configured to inhibit the escape of gas from the pipeline 20, it is understood that some trace amounts of gas from the pipeline 20 may enter the ambient environment.

In order to move the camera 12 up and down the pipeline 20, a motor arrangement 41 is provided. The motor arrangement 41 includes a motor 42, which is connected to a gearbox 44. As explained more fully below, the gearbox 44 contains a number of rollers for facilitating movement of the push rod 14 into and out of the pipeline 20. As shown in FIG. 1, the motor arrangement 41 is attached directly to the entry tube 28; this assembly provides a number of advantages. First, there is no need for a separate support structure for the motor arrangement 41; rather, it is attached to existing portions of the inspection system 10. In addition, having the motor arrangement 41 in close proximity to the first end of the entry tube 28, allows the push rod 14 to be moved forward and backward in the pipeline 20 without the need for an operator to feed the push rod 14 at the point of entry. Thus, an operator may actuate the motor 42 remotely, which provides a number of advantages over existing inspection systems. First, use of the motor arrangement 41 allows a single operator to effectively use the inspection system 10. Secondly, the operator can actuate the motor 42 from a safe distance away from the opening in the pipeline 20. In addition, the use of the motor arrangement 41 provides for controlled, precise movement of the camera 12 up and down the pipeline 20, thereby increasing the accuracy of the inspection and the ease with which it is carried out.

The gearbox 44 includes openings 46, 48 which allow the push rod 14 to pass therethrough. Also shown in FIG. 1 are handles 50, 52 attached to the entry tube 28. The handles 50, 52 allow the operator to adjust the entry tube 28 up and down based on the diameter of the pipeline being inspected. The motor arrangement 41 is attached to the entry tube 28 via a clamp arrangement 54, which allows the motor arrangement 41 to be completely removed from the entry tube 28. This helps to facilitate positioning of the entry tube 28 within a pipeline, such as the pipeline 20. The operator merely loosens the clamp arrangement 36, adjusts the height of the entry tube 28 using the handles 50, 52, and then secures the position of the entry tube 28 by locking the clamp arrangement 36.

FIG. 2 shows a partial fragmentary side view of a portion of the inspection system 10. As shown in FIG. 2, the gearbox 44 includes first and second halves 56, 58 which are held together with fastening arrangements 60, 62. Having the gearbox 44 split in this manner facilitates set up of the inspection system 10. For example, to insert the camera 12 into the pipeline 20, the cap 40 on the entry tube 28 is loosened to allow the camera 12 and the positioning system 22 to pass through the packing gland under the cap 40 and into the entry tube 28. This may conveniently take place prior to the motor arrangement 41 being attached to the entry tube 28.

Prior to the motor arrangement 41 being attached to the entry tube 28, the first and second halves 56, 58 can be opened by loosening nuts 64, 66 on the fastening arrangements 60, 62. This allows eye bolts 68, 70 to be pivoted to allow the first and second halves 56, 58 of the gearbox 44 to be swung open on a hinge (not shown). The push rod 14 can then be placed between pairs of rollers 72, 74; 76, 78; and 80, 82. The motor 42 can be configured with a gear or gears to drive at least one of the rollers, such as the roller 74 shown in FIG. 2. In this way, the rollers 72-82 may be driving members, or they may merely act as guides, depending on the particular arrangement within the gearbox 44. As shown in FIG. 2, a second end 84 of the second conduit 30 is configured for attachment to the valve system 24. In the embodiment shown in FIG. 2, the second conduit 30 is welded to a plate 86 which cooperates with the valve system 24 to ensure that a seal is maintained even in the presence of high-pressure gas within the pipeline 20.

Also shown in FIG. 2, the entry tube 28 includes a second end 88 and a transition member, or guide shoe 90, disposed proximate to the second end 88. The guide shoe 90 facilitates a change in direction of the push rod 14 as it enters the pipeline 20 from within the entry tube 28. As shown in FIG. 2, the entry tube 28 has a generally round cross-section, having a diameter (D). The guide shoe 90 is configured so that it does not extend beyond the outer diameter (D) of the entry tube 28, which allows the entry tube 28 to be inserted through a relatively small hole in the pipeline 20, without interference from the guide shoe 90. In order to facilitate entry of the camera 12, the entry tube 28 includes an open channel 92 proximate to its second end 88. As shown in FIG. 2, the guide shoe 90 forms one end of the channel 92.

FIG. 3 shows a portion of the entry tube 28, and in particular a portion near the second end 88. As shown in FIG. 3, the guide shoe 90 has a first surface 94 and a second surface 96 generally opposite the first surface 94. The second surface 96 is generally convex, which helps to increase the contact between the second surface 96 and a generally concave interior surface 98 of the pipeline 20 (see FIG. 2). As shown in FIG. 2, the first surface 94 of the guide shoe 90 forms an oblique angle with a first longitudinal axis 100 of the pipeline 20. It also forms an oblique angle with a second longitudinal axis 102 of the entry tube 28.

In the embodiment shown in FIG. 2, the first and second longitudinal axes 100, 102 form an oblique angle with each other. For example, if the pipeline 20, and therefore its longitudinal axis 100, is generally horizontal, then the entry tube 28, and its longitudinal axis 102, are not oriented vertically. Rather, the entry tube 28 is provided with an angle of approximately 20° away from vertical, which helps to facilitate entry of the camera 12 and push rod 14 into the pipeline 20.

The present invention does, however, contemplate orienting an entry tube, such as the entry tube 28, vertically to a horizontal pipeline. This may be convenient when a method such as keyholing is used to access the pipeline. Keyholing attempts to minimize the concrete and/or soil removal required to access the pipeline; therefore, the access hole diameter is relatively small. When keyholing is used, it may not be practical to orient an entry tube, such as the entry tube 28, at an angle away from vertical. In such a case, the present invention can be configured with an entry tube whose longitudinal axis is 90° from the longitudinal axis of the pipeline it is entering. This is possible, in part, because of the use of a guide shoe, such as the guide shoe 90. Even if the entry tube 28 were oriented such that the axis 102 was 90° from the axis 100, the guide shoe 90 would provide a smooth transition for the camera 12 and push rod 14 from its initial orientation parallel to the entry tube 28, to its later orientation generally parallel to the pipeline 20.

As shown in FIG. 2, the pipeline 20 is large enough that the positioning system 22 does not contact the top and bottom of the interior surface 98. Rather, in such a large pipeline, such as the pipeline 20, the positioning system 22 merely keeps the camera 12 from dragging along the bottom of the interior surface 98. FIG. 4 shows an example of the camera 12 and the positioning system 22 inside a pipeline 104 having a smaller diameter than the pipeline 20 shown in FIG. 2. As shown in FIG. 4, the positioning system 22 keeps the camera 12 generally centered within the interior of the pipeline 104. The positioning system 22 includes a plurality of flexible arms 106, 108. Although it is possible to configure a positioning system, such as the positioning system 22, with only two flexible arms, the positioning system 22, in fact, has three flexible arms 106, 108, 110 (see FIG. 5).

As discussed above, the positioning system 22 is automatically deployable as it exits the entry tube 28 into a pipeline, and is automatically retractable as it leaves the pipeline and returns to the entry tube 28. The automatic deployment and retraction of the positioning system 22 is particularly beneficial in applications involving high-pressure gas pipelines, where it is desirable to have little or no interaction between an operator and an open pipeline. As shown in FIG. 4, each of the arms 106, 108 (and the arm 110 not visible in FIG. 4) has pivotal attachments 112, 114 at a first end 116 of the camera 12. Each of the arms 106, 108 (and 110) also has pivotal attachments 118, 120 at a biasing member 122. In the embodiment shown in FIG. 4, the biasing member 122 is a coil spring which is disposed adjacent a first end 124 of the push rod 14. The spring 122 has a first end 126 axially fixed relative to the first end 124 of the push rod 14. In particular, the first end 126 is axially fixed by an adapter member 128 which is attached to the first end 124 of the push rod 14.

FIG. 6 shows a side view of the adapter 128, including two threaded apertures 130, 132. The adapter 128 may be made in two halves, such that the first end 124 of the push rod 14 can be inserted into an opening 134 between the two halves of the adapter 128, and threaded fasteners (not shown) can be used to tighten the two halves of the adapter 128 to secure the push rod 14 therebetween. Also shown in FIG. 6, the adapter 128 includes a second opening 136 which is configured to receive one end of a support member 138 (see FIG. 4). As with the first end 124 of the push rod 14, the adapter 128 can be clamped down on the support member 138 after the spring 122 is installed on the outside surface 140 of the adapter 128. Returning to FIG. 4, it is shown that the support member 138 is disposed between the first end 124 of the push rod 14 and the first end 116 of the camera 12. The support member 138 supports the camera 12 remotely from the first end 124 of the push rod 14, and thereby provides a distance between them to facilitate use of the positioning system 22.

As noted above, the spring 122 has a first end 126 that is axially fixed relative to the first end 124 of the push rod 14. Conversely, a second end 142 of the spring 122 is axially movable relative to the first end 124 of the push rod 14. As shown in FIG. 4, the pivotal attachments 118, 120 include apertures 144, 146 through the flexible arms 106, 108. Each of the apertures 144, 146 has a coil 148 of the spring 122 disposed therethrough. The coil 148 is near the movable end 142 of the spring 122. This facilitates the automatic deployment and retraction of the positioning system 22.

In particular, as the camera 12 and positioning system 22 leave the relatively small diameter of the entry tube 28 and enter the pipeline 104, the second end 142 of the spring 122 moves away from the first end 126 of the spring 122. This facilitates an automatic outward movement of the arms 106, 108 (and 110) toward an interior surface 150 of the pipeline 104. Similarly, when the positioning system 22 is retracted into the smaller diameter entry tube 28, an inward force is exerted on the arms 106, 108, 110 which forces the second end 142 of the spring 122 closer to the first end 126 of the spring 122. This means that the positioning system 22 can be automatically deployed from the smaller diameter entry tube 28 into a larger diameter pipeline, such as the pipeline 104, without any interaction from a system operator. Similarly, no action is required to retract the positioning system 22, other than the retraction of the push rod 14 back into the entry tube 28.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An inspection system for inspecting a pressurized gas pipeline, the inspection system comprising:
 an elongate flexible guide member;
 a first conduit having first and second ends, the first conduit being configured for sealed insertion into the pipeline such that the first end is outside the pipeline, the second end is inside the pipeline, and escape of gas from inside the pipeline is inhibited as the second end is inserted into the pipeline, the first conduit being further configured to receive the guide member therein, thereby facilitating entry of the guide member into the pipeline;
 a second conduit configured for sealed attachment to the pipeline at an opening in the pipeline, and further configured to receive the first conduit therein, thereby facilitating entry of the first conduit into the pipeline through the opening;
 a first seal cooperating with the first conduit and the guide member to inhibit gas from the pipeline from escaping through an inside of the first conduit;
 a second seal cooperating with the first and second conduits for effecting the sealed insertion of the first conduit into the pipeline;
 a transition member adjacent the second end of the first conduit for facilitating a change in direction of the guide member as the guide member enters the pipeline from within the first conduit; and
 a camera attached to the guide member and configured to pass through the first conduit and into the pipeline.

2. The inspection system of claim 1, wherein at least a portion of the first conduit has a generally round cross section defining an outer diameter, thereby allowing the first conduit to be inserted through a generally round entry hole in the pipeline, and
 wherein the transition member is attached to the first conduit and configured to not extend beyond the outer diameter of the first conduit, thereby allowing the first conduit to be inserted into the pipeline through the entry hole without interference from the transition member.

3. The inspection system of claim 2, wherein the first conduit includes an open channel proximate the second end, the transition member forming one end of the channel.

4. The inspection system of claim 1, wherein the transition member has a first surface and a second surface generally opposite the first surface, the first surface being configured to provide a contact surface for the camera as the camera leaves the first conduit and enters the pipeline, at least a portion of the second surface being generally convex, thereby increasing contact between the second surface and a generally concave interior surface of the pipeline.

5. The inspection system of claim 1, the pipeline defining a first longitudinal axis, and wherein the first conduit defines a second longitudinal axis, and the first conduit is configured for insertion into the pipeline such that the first and second longitudinal axes form an oblique angle with each other, thereby further facilitating entry of the guide member into the pipeline.

6. The inspection system of claim 1, further comprising a motor operable to move the guide member through the first conduit and into the pipeline, the motor being disposed proximate the first end of the first conduit to facilitate remote feeding of the guide member through the first conduit.

7. The inspection system of claim 1, further comprising an automatically deploying and retracting positioning system disposed between the camera and one end of the guide member for positioning the camera away from an inner surface of the pipeline.

8. The inspection system of claim 7, wherein the positioning system includes:
 a plurality of flexible arms, each of the arms being deployable in a direction away from the camera toward the inner surface of the pipeline, and
 a biasing member configured to exert a force on one end of each of the arms, thereby facilitating the automatic deployment of the arms.

9. The inspection system of claim 8, wherein one end of each of the arms is pivotally attached to the biasing member adjacent one end of the biasing member, thereby facilitating axial movement of the one end of the biasing member when an inward force is applied to the arms.

10. The inspection system of claim 1, further comprising:
 a reel for dispensing and retracting the guide member; and
 a monitor in communication with the camera and attached to the reel for remotely providing images captured by the camera.

* * * * *